(12) United States Patent
Bremer et al.

(10) Patent No.: US 11,735,311 B2
(45) Date of Patent: Aug. 22, 2023

(54) UNIVERSAL IMAGE REPRESENTATION BASED ON A MULTIMODAL GRAPH

(71) Applicant: Lawrence Livermore National Security, LLC, Livermore, CA (US)

(72) Inventors: Peer-Timo Bremer, Livermore, CA (US); Rushil Anirudh, Dublin, CA (US); Jayaraman Jayaraman Thiagarajan, Milpitas, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 24 days.

(21) Appl. No.: 17/470,331

(22) Filed: Sep. 9, 2021

(65) Prior Publication Data

US 2022/0181006 A1 Jun. 9, 2022

Related U.S. Application Data (62) Division of application No. 16/684,388, filed on Nov. 14, 2019, now Pat. No. 11,145,403.

(51) Int. Cl.
*G06K 9/00* (2022.01)
*G16H 30/20* (2018.01)
(Continued)

(52) U.S. Cl.
CPC .............. *G16H 30/20* (2018.01); *G06N 3/08* (2013.01); *G06N 20/10* (2019.01); *G06T 7/0014* (2013.01); *G06T 2207/20081* (2013.01); *G06T 2207/20084* (2013.01); *G06T 2207/30024* (2013.01); *G06T 2207/30236* (2013.01)

(58) Field of Classification Search
CPC ........ G16H 30/20; G16H 50/20; G16H 30/40; G06N 20/10; G06N 3/08; G06N 3/045; G06T 2207/30096; G06T 7/0012; G06T 7/0014; G06T 2207/20081; G06T 2207/20084; G06T 2207/30024; G06T 2207/30236

See application file for complete search history.

(56) References Cited

U.S. PATENT DOCUMENTS

| 2019/0073594 | A1* | 3/2019 | Eriksson | ............... G06F 18/23 |
| 2019/0148021 | A1* | 5/2019 | Styner | ................... G06N 20/10 |
| | | | | 705/2 |

(Continued)

*Primary Examiner* — Xin Jia
(74) *Attorney, Agent, or Firm* — Perkins Coie LLP (57) ABSTRACT

A system for classifying a target image with segments having attributes is provided. The system generates a graph for the target image that includes vertices representing segments of the image and edges representing relationships between the connected vertices. For each vertex, the system generates a subgraph that includes the vertex as a home vertex and neighboring vertices representing segments of the target image within a neighborhood of the segment represented by the home vertex. The system applies an autoencoder to each subgraph to generate latent variables to represent the subgraph. The system applies a machine learning algorithm to a feature vector comprising a universal image representation of the target image that is derived from the generated latent variables of the subgraphs to generate a classification for the target image.

21 Claims, 9 Drawing Sheets

(51) Int. Cl.
  *G06N 3/08*   (2023.01)
  *G06N 20/10*  (2019.01)
  *G06T 7/00*   (2017.01)

(56) References Cited

U.S. PATENT DOCUMENTS

2020/0142957 A1* 5/2020 Patra .................. G06N 3/04
2020/0257982 A1* 8/2020 Kim ................... G06N 3/047
2020/0363815 A1* 11/2020 Mousavian ............ G06N 3/045

* cited by examiner

UNIVERSAL IMAGE REPRESENTATION BASED ON A MULTIMODAL GRAPH

CROSS-REFERENCE TO RELATED APPLICATION

This application is a divisional of U.S. patent application Ser. No. 16/684,388 filed on Nov. 14, 2019, which is hereby incorporated by reference in its entirety.

STATEMENT REGARDING FEDERALLY SPONSORED RESEARCH

This invention was made with Government support under Contract No. DE-AC52-07NA27344 awarded by the United States Department of Energy. The Government has certain rights in the invention.

BACKGROUND

In many environments, there is a need to process images based on characteristics of regions of interest (i.e., segments) within the images. The images may be processed to support a wide variety of image analysis tasks, such as object detection, classification, and regression. For example, in a medical environment, an image generated from a scan (e.g., computed tomography ("CT") scan) of a patient may need to be analyzed to generate a classification based on whether the patient has a tumor and the aggressiveness of the tumor growth. As another example, an image of a cell culture of a patient with cancer may need to be analyzed to generate a classification based on the aggressiveness of the cancer, the prognosis for the patient, the efficacy of a treatment, and so on. As another example, an image in which an animal appears may need to be analyzed to detect the presence of the animal or determine what type of animal it is. The processing of images is useful in a wide range of other applications such as analysis of military activity, crop diseases in agricultural fields, crowds of people, transportation patterns, forestry management, and so on.

A convolutional neural network ("CNN") is a type of neural network that has been developed specifically to perform image analysis tasks. As an example, a CNN may be used to input an entire image and output a classification for the image. For example, a CNN can be used to automatically determine whether a scan of a patient indicates the presence of a tumor. A CNN has multiple layers such as a convolutional layer, a rectified linear unit ("ReLU") layer, a pooling layer, a fully connected ("FC") layer, and so on. Some more complex CNNs may have multiple convolutional layers, ReLU layers, pooling layers, and FC layers.

Although CNNs are effective at image analysis tasks, the training of a CNN can be computationally very expensive. For example, a high-resolution 3D image may contain 134,217,728 pixels (i.e., $512^3$ pixels). If the convolutional layer includes eight filters, the convolutional layer may include 1,073,741,824 nodes. During training, each image of the training data will need to be input to the CNN multiple times and convolutional windows processed for each image as the weights for the nodes of the convolution layer and the FC layer are learned. Because the number of degrees of freedom and the number of images is typically very large, it would be impracticable to train such a CNN.

Over time, as image analysis tasks involve analyzing more complex relationships within images, CNNs may require an exponentially increasing number of images (referred to as training data) to learn the complex relationships necessary to perform the task. For example, to diagnose a cancer from a microscopy image of a cell culture, the analysis of the relative position of cells and their spatial arrangement might be crucial. Unfortunately, the training of a CNN to classify all possible positions and arrangements presents problems because it requires such vast amounts of training data as to make the training infeasible. Similar problems exist in the performing of image analysis tasks for other applications. One example application is the processing of overhead imagery of cities, where cars and people form a complex arrangement, to identify overall trends such as commuting trends. Another problem with use of CNNs is that each application may require design of a custom CNN architecture. The designing of a custom CNN architecture may require an expert in machine learning, and such experts may be in short supply.

DETAILED DESCRIPTION

A universal image representation ("UIR") system is provided that employs a multimodal graph derived from an image to generate a universal image representation of the image. In some embodiments, to generate a universal image representation for a target image, the UIR system inputs the target image and attributes associated with segments of the target image. For example, when the target image is of a cell culture, the segments may be cells and an attribute may indicate expression level of a protein. The UIR system performs a segmentation of the target image to identify segments that satisfy a segment criterion. Continuing with the example, the segment criterion specifies features of an image that are characteristics of a cell. After the segments are identified, the UIR system then creates a graph with vertices representing segments and edges representing relationships between segments represented by the vertices connected by the edges. For example, the graph may include a vertex for each segment and an edge for each pair of vertices that satisfies an edge criterion, such as the represented segments being within a threshold distance of each other. The UIR system also associates (or tags) each vertex with the attributes (e.g., assigned by a medical technician) of the segment that the vertex represents. Continuing with the cell culture example, each vertex is associated with an attribute indicating the expression level of a protein in the represented segment (i.e., cell). The graph with the associated attributes is a multimodal graph. The UIR system then, for vertices of the graph, identifies a subgraph of the graph. A subgraph includes a home vertex representing a home segment and includes vertices in the neighborhood of the home vertex that satisfy a neighborhood criterion, such as the segments represented by the vertices being adjacent to (e.g., within a threshold distance of) the home segment. The UIR system then inputs each subgraph into an autoencoder to generate latent variables (or hidden features) that are a representation of the subgraph. (An autoencoder and the training of an autoencoder are described below.) The universal image representation ("UIR") of the image is derived from the latent variables of the subgraphs. For example, the UIR may be a collection of the latent variables or may be derived from the latent variables by applying to the latent variables a function that implements a mathematical algorithm such as principal component analysis.

The UIR of a target image, rather than the target image itself, can be input to a machine learning algorithm to generate a label (e.g., a classification) for the target image. For example, when the target image is of a cell culture, the label may be an indication of the aggressiveness of the cancer, the prognosis for a patient (e.g., life expectancy), the efficacy of a treatment, and so on. A classifying machine learning algorithm ("CMLA") system implements a machine learning algorithm, which can be based on any of a variety of supervised or unsupervised machine learning techniques, such as a neural network (e.g., non-convolutional), a support vector machine, a Bayesian network, and so on, as well as combinations of machine learning techniques. (The training of a CMLA is described below.) A combination of the UIR system and the CMLA system that generate labels for target images is referred to as a UIR Classification ("UIRC") system.

The UIRC system thus allows machine learning algorithms that are not CNNs to be used to analyze images. As result, the UIR system overcomes shortcomings of CNNs such as the need for development of custom CNN architectures, the shortage of experts to customize CNNs, the computational expense of training and retraining CNNs, and so on.

In some embodiments, the UIR system trains an autoencoder using autoencoder training data that is derived from attributed image training data that includes images and the attributes of the segments within the images. The UIR system generates autoencoder training data in a manner similar to the generating of the subgraphs for a target image as described above. For each image of the attributed training data, the UIR system segments the image, generates a graph with vertices representing segments and edges representing relationships between the represented segments, associates attributes of the segments with the vertices, and generates subgraphs of the graph. The autoencoder training data may include, for each image, the subgraphs of the image. The UIR system then trains the autoencoder with the autoencoder training data. The autoencoder may include pre-layers of nodes, a latent variable layer of nodes, and a post-layer of nodes. The UIR system trains the autoencoder to learn weights for the nodes. Then, to generate the latent variables for a target image, the UIR system, for each subgraph of the target image, applies the weights of the pre-layers to the subgraph to generate the latent variables for the subgraph. The UIR of the target image is based on the latent variables of all the subgraphs.

In some embodiments, the UIRC system trains the CMLA using CMLA training data. The CMLA training data is a collection of CMLA training images and the attributes for the segments of the images along with a classification for each image. The UIRC system employs the UIR system to generate subgraphs with vertices associated with attributes for each CMLA training image. For each CMLA training image, the UIRC system then applies the autoencoder to each subgraph of the UIR training image to generate latent variables representing that image. The CMLA training data for the CMLA is, for each CMLA training image, a feature vector that includes the UIR for that image labeled with the classification for that image. The UIRC system then employs the CMLA system to train the CMLA using conventional machine learning training techniques appropriate for the type of CMLA (e.g., support vector machine). The CMLA training images may be the same as the UIR training images used to train the autoencoder or may be a different collection of images.

Figure 1:
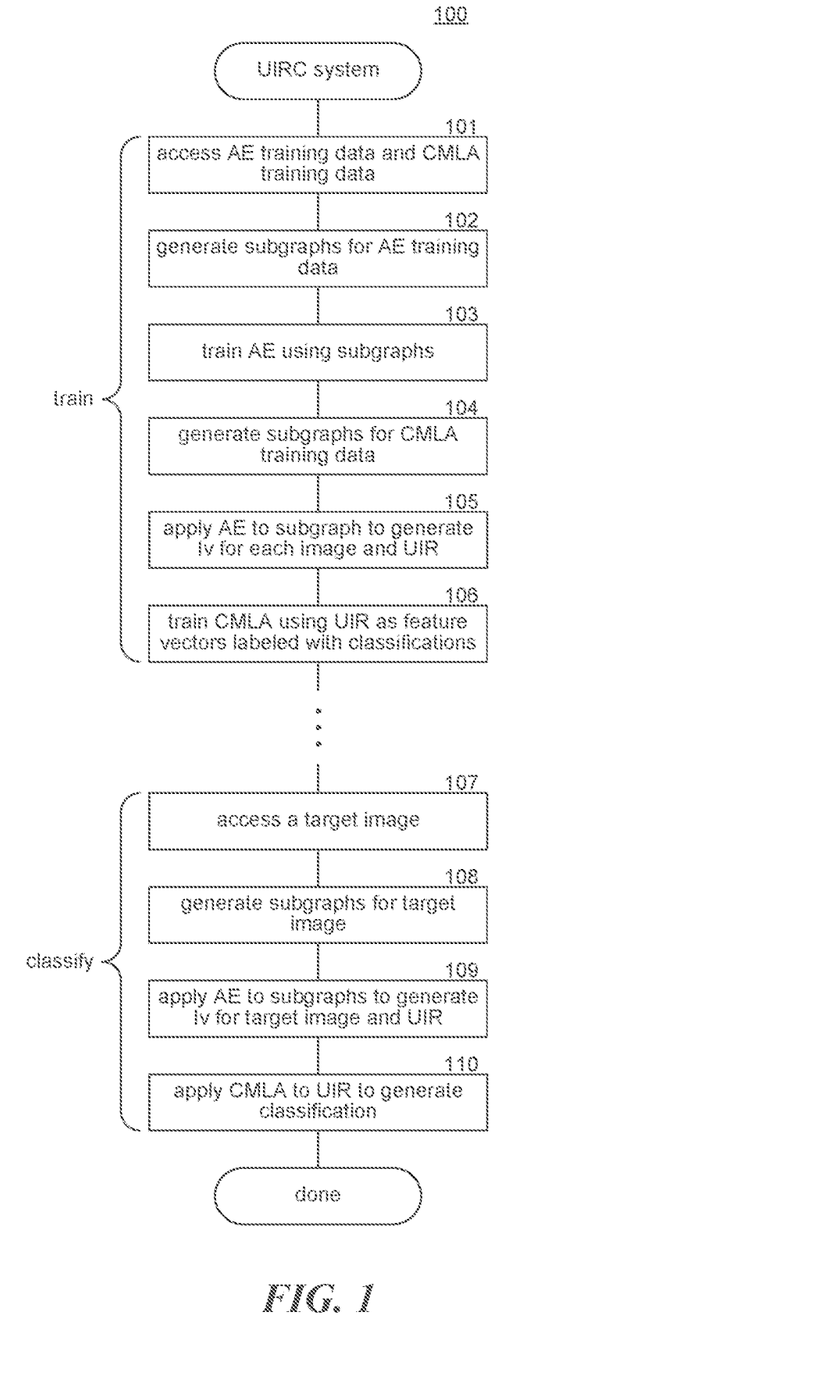
FIG. 1 is a flow diagram that illustrates the overall processing of the UIRC system in some embodiments.

FIG. 1 is a flow diagram that illustrates the overall processing of the UIRC system in some embodiments. The UIRC system 100 trains an autoencoder ("AE") using AE training data and a CMLA using CMLA training data that includes CMLA images. The UIRC system then classifies a target image using the autoencoder and the CMLA. In blocks 101-106, the UIRC system trains an autoencoder and a CMLA. In block 101, the UIRC system accesses the AE training data and the CMLA training data. In block 102, the UIRC system generates subgraphs of each image of the AE training data. Each vertex of a subgraph is associated with one or more attributes of the segment that the vertex represents. In block 103, the UIRC system trains the autoencoder using the subgraphs. In block 104, the UIRC system generates subgraphs for each image of the CMLA training data. In block 105, the UIRC system applies the autoencoder to the subgraphs of each image of the CMLA training data to generate latent variables ("lv") for each image and then generates a UIR for each image based on the latent variables. In block 106, the UIRC system trains the CMLA using, for each CMLA image, the UIR for that image as a feature vector that is labeled with the classification of that image. In blocks 107-110, the UIRC system uses the trained autoencoder and the trained CMLA to classify a target image. In block 107, the UIRC system accesses the target image along with the attributes of its segments. In block 108, the UIRC system generates subgraphs for the target image with each vertex associated with the attribute of the segment that the vertex represents. In block 109, the UIRC system applies the autoencoder to the subgraphs to generate latent variables for the target image and then generate a UIR for the target image based on the latent variables. In block 110, the UIRC system applies the CMLA to a feature vector containing the UIR to generate a classification for the target image.

Figure 2:
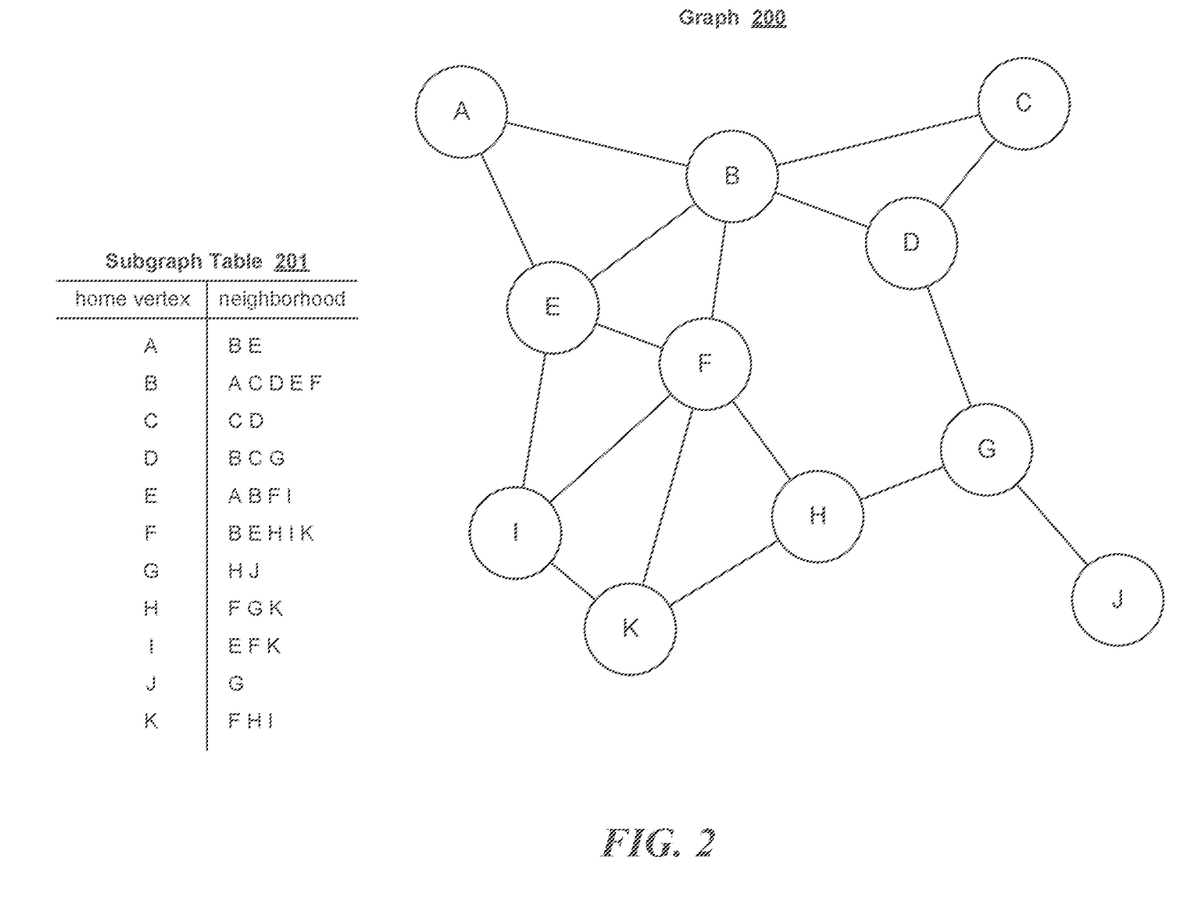
FIG. 2 is a graph that represents an image.

FIG. 2 is a graph that represents an image. The graph 200 includes vertices A-K representing 11 segments of the image. The edges between the vertices satisfy an edge criterion based on adjacency between the vertices. For example, there is an edge between vertex A and vertex B, indicating that they are adjacent. In contrast, there is no edge between vertex A and vertex C, indicating that they are not adjacent. Various edge criteria may be used to define when vertices are to be connected by edges. For example, an edge criterion may be based on distance between segments represented by vertices, attributes of vertices, and so on. The subgraph table 201 identifies the subgraphs for each vertex of the graph. For example, the subgraph for home vertex A comprises vertices B and E. The subgraph for home vertex E comprises vertices A, B, F, and I. Various subgraph (neighborhood) criteria may be used to define the subgraph for a home vertex. For example, the subgraph table 201 is based on a subgraph criterion of adjacency. Another subgraph criterion may be based on vertices that are within a distance of two edges from a home vertex. In some cases, a subgraph may have only a home vertex and might not be used for training the autoencoder or classifying a target image.

Figure 3:
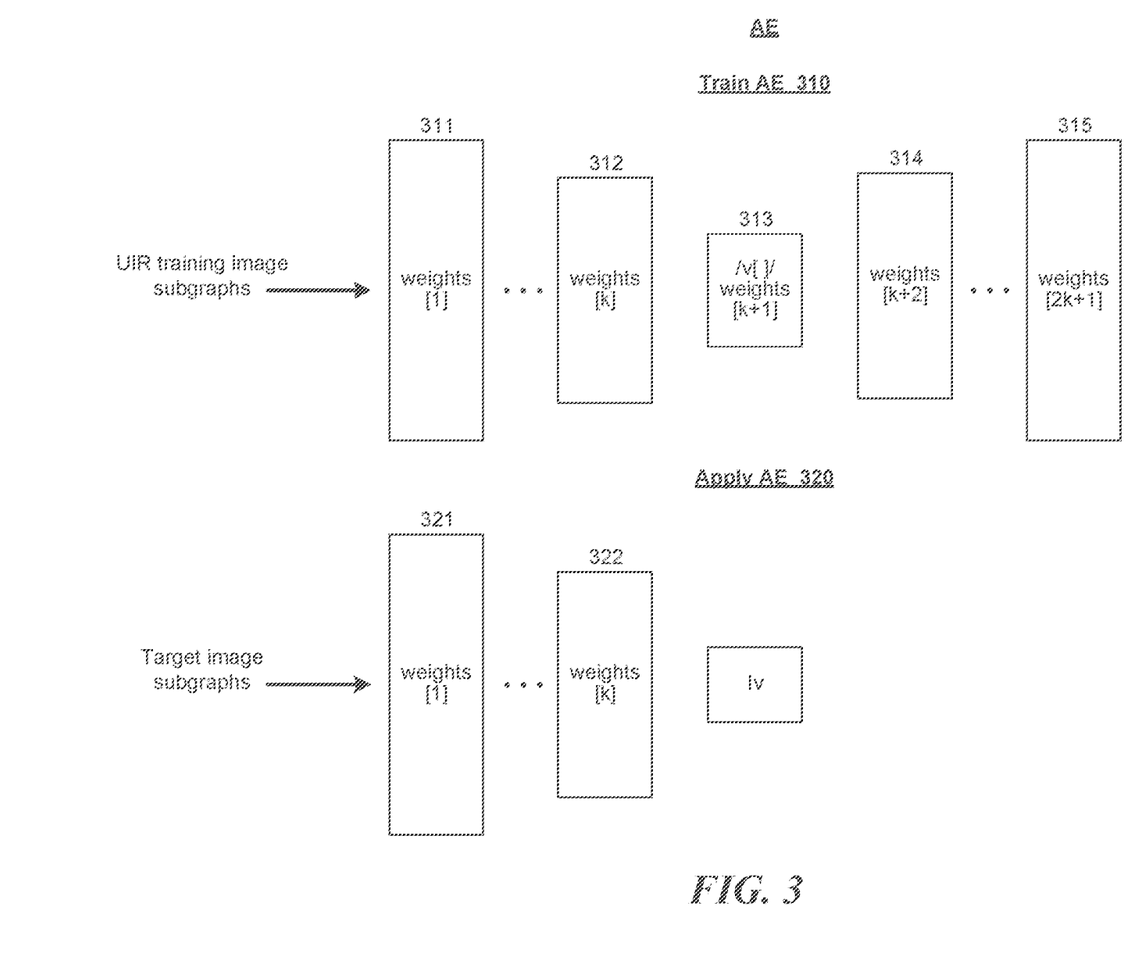
FIG. 3 illustrates an autoencoder architecture for training and for applying the autoencoder in some embodiments.

FIG. 3 illustrates an autoencoder architecture for training and for applying the autoencoder in some embodiments. The train autoencoder architecture 310 includes pre-layers 311-312, a latent variable layer 313, and post-layers 314-315. The pre-layers may include a decreasing number of nodes at each subsequent pre-layer. The latent variables layer includes a node for each latent variable. The post-layers may include an increasing number of nodes at each subsequent post-layer. The first pre-layer and the last post-layer, the second pre-layer and the second-to-last post-layer, and so on may have the same number of nodes. The apply autoencoder architecture 320 includes pre-layers 321-322 corresponding to pre-layers 311-312 having weights learned during training of the autoencoder for each node. To generate the latent variables for target image, the weights of pre-layers 321-322 are applied to the subgraphs for the target image.

Figure 4:
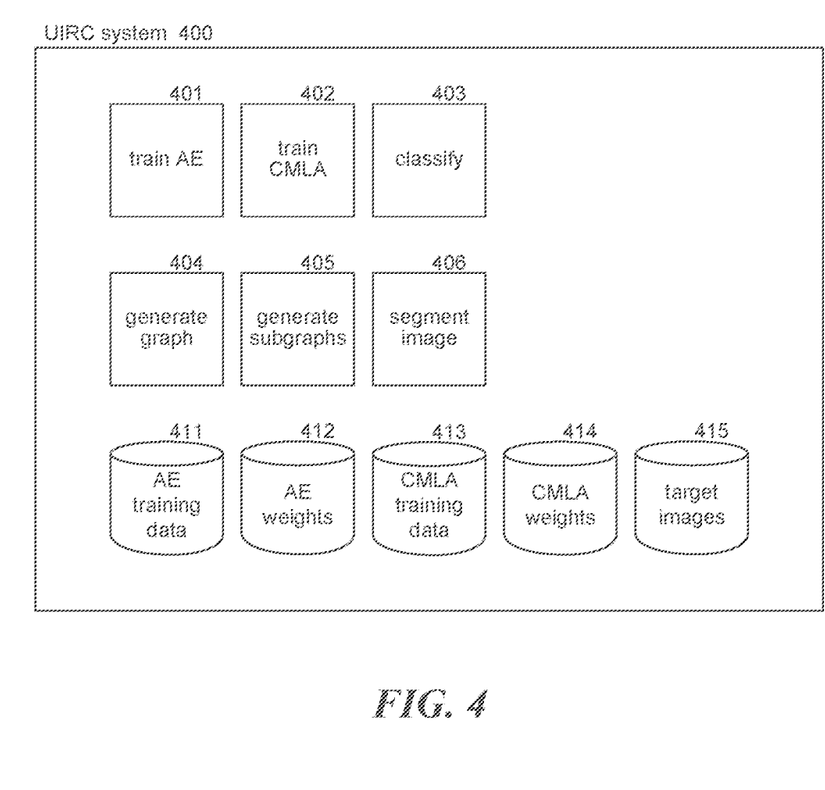
FIG. 4 is a block diagram that illustrates components of the UIRC system in some embodiments.

FIG. 4 is a block diagram that illustrates components of the UIRC system in some embodiments. The UIRC system includes a train autoencoder component 401 of the UIR system, a train CMLA component 402 of the CMLA system, a classify component 403 of the CMLA, a generate graph component 404, a generate subgraphs component 405, and a segment image component 406. The UIRC system also includes an AE training data store 411, an autoencoder weights data store 412, a CMLA training data store 413, a CMLA weights store 414, and a target images store 415. The train autoencoder component is invoked to train an autoencoder using the AE training data. The train CMLA component is invoked to train the CMLA using the CMLA training data. The classify component is invoked to generate a classification for a target image. The segment image component generates a segmentation of an image. The generate graph component generates a graph based on segments of an image. The generate subgraphs component generates subgraphs of a graph.

The computing devices and systems on which the UIR system may be implemented may include a central processing unit, input devices, output devices (e.g., display devices and speakers), storage devices (e.g., memory and disk drives), network interfaces, graphics processing units, accelerometers, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing devices may include desktop computers, laptops, tablets, e-readers, personal digital assistants, smartphones, gaming devices, servers, and computer systems, such as massively parallel systems. The computing devices may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and include other storage means. The computer-readable storage media may have recorded upon or may be encoded with computer-executable instructions or logic that implements the UIR system. The data transmission media is used for transmitting data via transitory, propagating signals or carrier waves (e.g., electromagnetism) via a wired or wireless connection.

The UIR system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various embodiments. Aspects of the system may be implemented in hardware using, for example, an application-specific integrated circuit ("ASIC").

Figure 5:
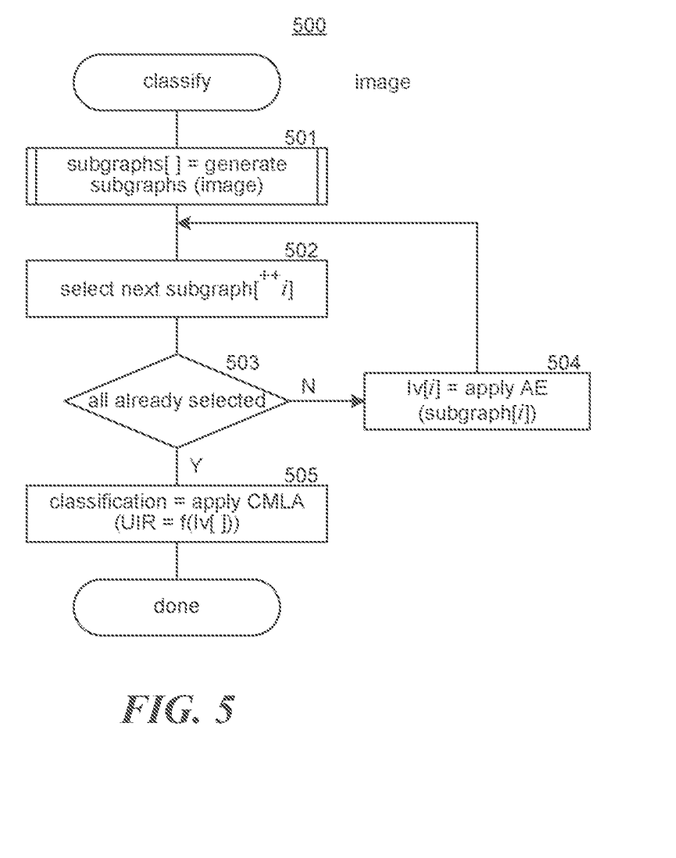
FIG. 5 is a flow diagram that illustrates processing of a classify component of the UIRC system in some embodiments.

FIG. 5 is a flow diagram that illustrates processing of a classify component of the UIRC system in some embodiments. The classify component 500 is invoked, passing a target image to be classified. In block 501, the component invokes a generate subgraphs component to generate subgraphs for the target image. In blocks 502-504, the component loops, applying the autoencoder to generate latent variables for each subgraph. In block 502, the component selects the next subgraph. In decision block 503, if all the subgraphs have already been selected, then the component continues at block 505, else the component continues at block 504. In block 504, the component applies the autoencoder to the selected subgraph to generate the latent variables for the subgraph. In block 505, the component applies the CMLA to a UIR derived by applying a function to the collection of latent variables to generate a classification for the target image and then completes.

Figure 6:
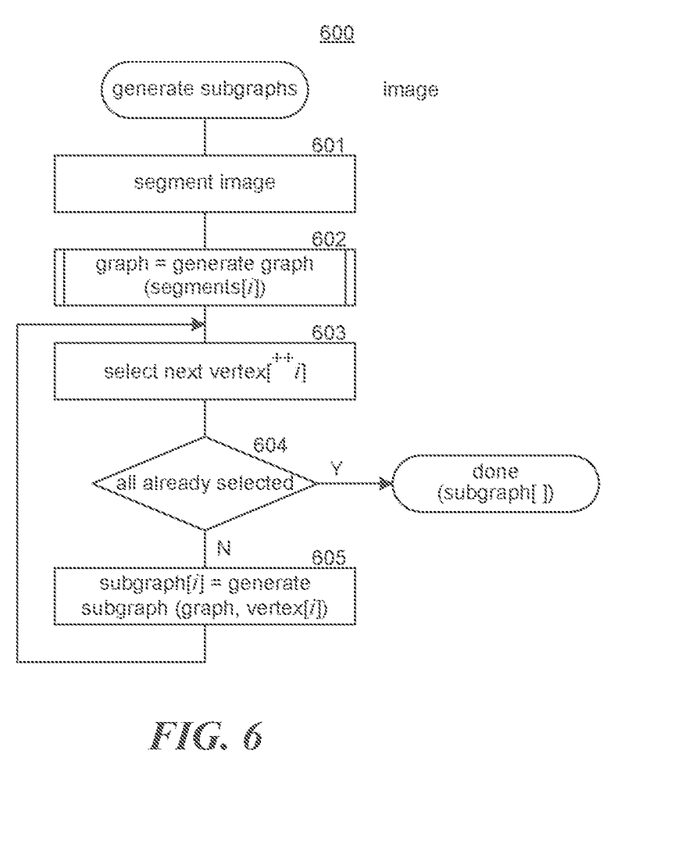
FIG. 6 is a flow diagram that illustrates the processing of a generate subgraphs component of the UIRC system in some embodiments.

FIG. 6 is a flow diagram that illustrates the processing of a generate subgraphs component of the UIRC system in some embodiments. The generate subgraphs component 600 is invoked, passing an image, and generates subgraphs for that image. In block 601, the component identifies the segments of the image. In block 602, the component invokes a generate graph component, passing the segments to generate a graph for the image. In blocks 603-605, the component loops, generating a subgraph for each vertex of the graph. In block 603, the component selects the next vertex of the graph. In decision block 604, if all the vertices have already been selected, then the component completes, else the component continues at block 605. In block 605, the component generates the subgraph of the graph for the selected vertex and then loops to block 603 to select the next vertex.

Figure 7:
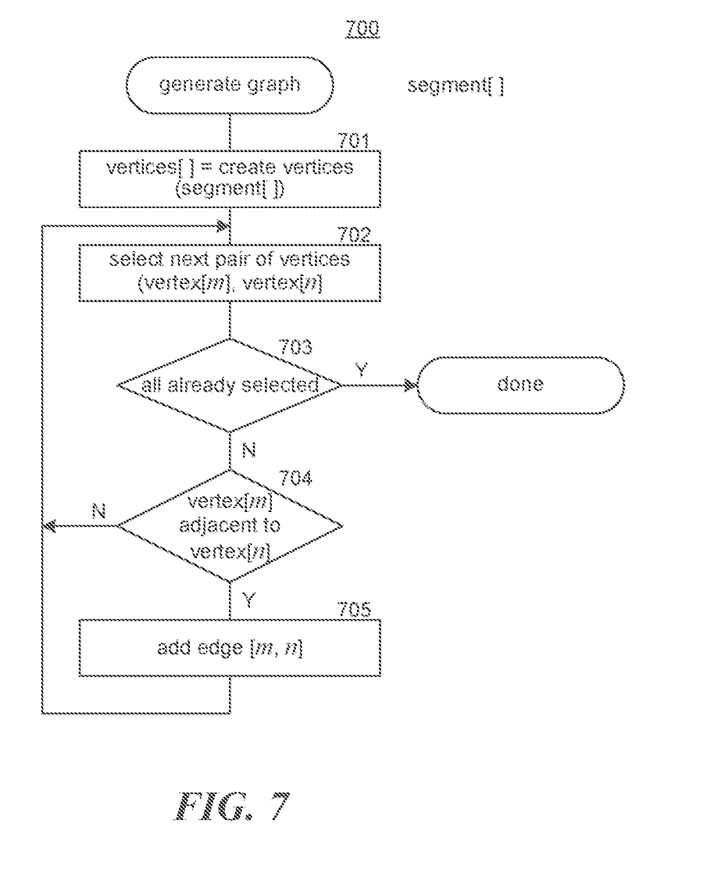
FIG. 7 is a flow diagram that illustrates the processing of a generate graph component of the UIRC system in some embodiments.

FIG. 7 is a flow diagram that illustrates the processing of a generate graph component of the UIRC system in some embodiments. The generate graph component 700 is passed an indication of a segmentation of an image that includes additional information for each segment such as location, size, and attributes. In block 701, the component creates a vertex for each segment and associates the attributes of that segment with the vertex. In block 702, the component selects the next pair of vertices. In decision block 703, if all the pairs of vertices have already been selected, then the component completes, else the component continues at block 704. In decision block 704, if the selected pair of vertices satisfies the edge criterion, then the component continues at block 705, else the component loops to block 702 to select the next pair of vertices. In block 705, the component adds an edge between the selected pair of vertices and then loops to block 702 to select the next pair of vertices.

Figure 8:
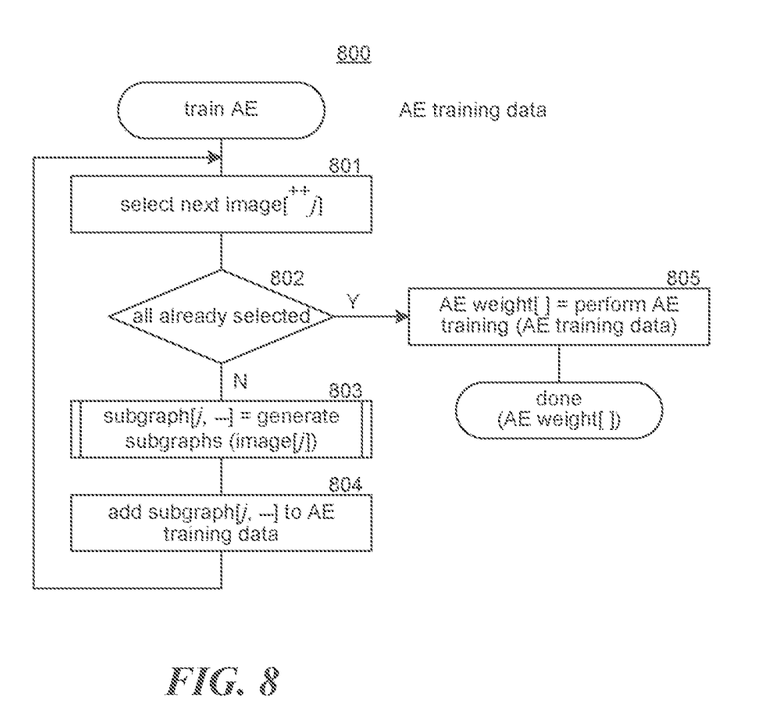
FIG. 8 is a flow diagram that illustrates the processing of a train autoencoder component of the UIRC system in some embodiments.

FIG. 8 is a flow diagram that illustrates the processing of a train autoencoder component of the UIRC system in some embodiments. The train autoencoder component 800 is passed AE training data that includes images and attributes associated with segments of the image. In block 801, the component selects the next image of the AE training data. In decision block 802, if all the images have already been selected, then the component continues at block 805, else the component continues at block 803. In block 803, the component invokes the generate subgraphs component to generate subgraphs for the selected image. In block 804, the component adds the subgraphs for the image to the AE training data and loops to block 801 to select the next image. In block 805, the component performs autoencoder training using the AE training data to generate AE weights. The component then completes.

Figure 9:
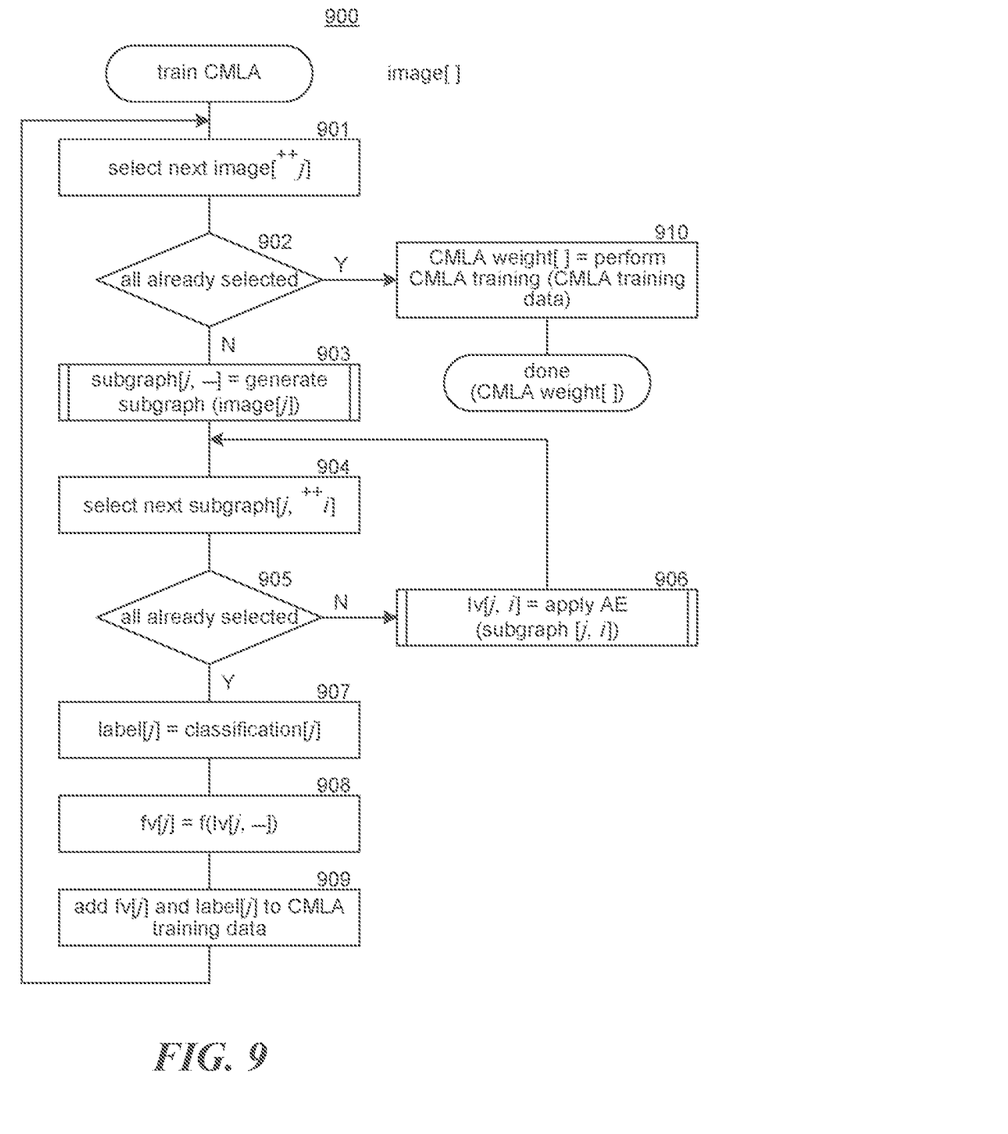
FIG. 9 is a flow diagram that illustrates the processing of a train CMLA component of the UIRC system in some embodiments.

FIG. 9 is a flow diagram that illustrates the processing of a train CMLA component of the UIRC system in some embodiments. The train CMLA component 900 is passed CMLA training data that includes images and attributes for the segments of the image and a classification for each image. In block 901, the component selects the next image. In decision block 902, if all the images have already been selected, then the component continues at block 910, else the component continues at block 903. In block 903, the component invokes a generate subgraphs component to generate subgraphs for the selected image. In block 904, the component selects the next subgraph of the selected image. In decision block 905, if all the subgraphs have already been selected, then the component continues at block 907, else the component continues at block 906. In block 906, the component applies the autoencoder to the selected subgraph to generate latent variables for the subgraph and loops to block 904 to select the next subgraph. In block 907, the component labels the latent variables for the selected image with the classification of the image. In block 908, the component sets the feature vector for the selected image to the UIR of the image that is generated by applying a function to the latent variables of the subgraphs of the image. In block 909, the component adds the feature vector and label for the selected image to the CMLA training data and loops to block 901 to select the next image. In block 910, the component performs CMLA learning using the CMLA training data to generate CMLA weights and then completes.

The following paragraphs describe various embodiments of aspects of the UIRC system. An implementation of the UIRC system may employ any combination of the embodiments. The processing described below may be performed by a computing system with a processor that executes computer-executable instructions stored on a computer-readable storage medium that implements the UIR system.

In some embodiment, a method performed by one or more computing systems for classifying a target image with segments having attributes is provided. The method identifies segments of the target image. The method generates a graph for the target image that includes vertices and edges. Each vertex represents a segment and each edge satisfying an edge criterion based on the vertices that the edge connects. Each vertex is assigned an attribute of the segment represented by the vertex. For each vertex, the method generates a subgraph that includes the vertex as a home vertex and neighboring vertices representing segments of the target image within a neighborhood of the segment represented by the home vertex. The vertices of the subgraph satisfy a neighborhood criterion. For each subgraph, the method applies an autoencoder to the subgraph to generate latent variables to represent the subgraph. The autoencoder is trained using subgraphs generated from images and attributes of segments of images of autoencoder training data. The method applies a machine learning algorithm to a feature vector derived from the generated latent variables of the subgraphs to generate a classification for the target image. The machine learning algorithm is trained using feature vectors representing latent variables and labels representing classifications. The latent variables are generated by applying the autoencoder to subgraphs for images and attributes of classification machine learning algorithm training data. In some embodiments, the segments satisfy a segment criterion. In some embodiments, the machine learning algorithm is a support vector machine. In some embodiments, the machine learning algorithm is a neural network. In some embodiments, the images are of cell cultures and the segments are cells, an attribute indicates whether the segment represented by a vertex is cancerous, and a classification indicates aggressiveness of cancer associated with the cell culture. In some embodiments, the images are of a roadway system and each segment is a section of a roadway, an attribute indicates whether the segment represented by a vertex is congested, and a classification indicates whether action is needed to alleviate the congestion. In some embodiments, the images are of crowds and each segment is a person, an attribute indicates whether the segment represented by a vertex is of a person on a tracking list, and a classification indicates likelihood that an undesirable activity is in progress. In some embodiments, the neighborhood criterion is based on distances between a segment represented by a home vertex and other segments. In some embodiments, the neighborhood criterion is based on segments adjacent to the segment represented by the home vertex. In some embodiments, the edges connect vertices represent adjacent segments and the neighborhood criterion is further based on edge distance from the home vertex. In some embodiments, the method further generates a universal image representation of the target images. The universal image representation is derived from the generated latent variables.

In some embodiments, one or more computing systems for generating a universal image representation of a target image having regions of interest labeled with attributes are provided. The one or more computing systems include one or more computer-readable storage mediums for storing computer-executable instructions and one or more processors for executing the computer-executable instructions stored in the one or more computer-readable storage mediums. The instructions identify segments of the target image that correspond to regions of interest. The instructions generate a graph that includes vertices and edges. Each vertex represents a segment and each edge representing a relationship between the segments represented by the vertices connected by the edge. The instructions generate a subgraph for each vertex that includes the vertex as a home vertex and neighboring vertices representing segments of the target image. The instructions apply an autoencoder to each subgraph to generate latent variables to represent the subgraph. The universal image representation of the target image is based on the latent variables of the subgraph. In some embodiments, the instructions include instructions to apply a machine learning algorithm to a feature vector comprising a universal image representation of the target image that is derived from the generated latent variables of the subgraphs to generate a classification for the target image. In some embodiments, each segment satisfies a segment criterion. In some embodiments, a neighboring vertex is identified based on distances between a segment represented by a home vertex and other segments. In some embodiments, a neighboring vertex is identified based on segments adjacent to the segment represented by the home vertex. In some embodiments, the edges connect vertices represent adjacent segments and a neighboring vertex is identified based on edge distance from the home vertex. In some embodiments, the autoencoder is trained using subgraphs generated from images and attributes of segments of images of autoencoder training data.

In some embodiments, a method performed by one or more computing systems for training an autoencoder to generate a universal image representation of a target image is provided. For each of a plurality of autoencoder training images, the method identifies segments of the autoencoder training image. Each segment is associated with an attribute. The method generates a graph that includes vertices and edges. Each vertex represents a segment and each edge representing a relationship between the segments represented by the vertices connected by the edge. The method generates a subgraph for each vertex that includes the vertex as a home vertex and neighboring vertices representing segments of the target image. The method then trains the autoencoder using the subgraphs as training data. The autoencoder is for generating latent variables. The universal image representation of the target image is derived from the latent variables. In some embodiments, the method further trains a machine learning algorithm for classification of images using training data that includes universal image representations of images and classifications of the images. In some embodiments, the images are of cell cultures and the segments are cells, an attribute indicates expression level of a protein the segment represented by a vertex, and a classification indicates aggressiveness of cancer associated with the cell culture. In some embodiments, the images are of a roadway system and each segment is a section of a roadway, an attribute indicates whether the segment represented by a vertex is congested, and a classification indicates whether action is needed to alleviate the congestion. In some embodiments, the images are of crowds and each segment is a person, an attribute indicates whether the segment represented by a vertex is of a person on a tracking list, and a classification indicates likelihood that an undesirable activity is in progress. In some embodiments, the method further generates a classification for a target image by: identifying segments of the target image, generating a graph with vertices representing segments and edges representing relationships between segments represented by the vertices that the edges connect, generating subgraphs of the graph, applying the autoencoder to each subgraph to generate latent variables for each subgraph, and applying the machine learning algorithm to a universal image representation of that target image that is derived from the latent variables to generate the classification for the target image. In some embodiments, the machine learning algorithm is a support vector machine. In some embodiments, the machine learning algorithm is a neural network. In some embodiments, the segments of an autoencoder training image satisfy a segment criterion. In some embodiments, the relationship is specified by an edge criterion satisfied by the segments represented by the vertices connected by the edge. In some embodiments, the vertices of a subgraph satisfy a neighborhood criterion that is based on segments adjacent to the segment represented by the home vertex. In some embodiments, the edges connect vertices representing adjacent segments and the neighborhood criterion is further based on edge distance from the home vertex.

In some embodiments, one or more computing systems for generating a classification for a target image are provided. The one or more computing systems include one or more computer-readable storage mediums for storing computer-executable instructions and one or more processors for executing the computer-executable instructions stored in the one or more computer-readable storage mediums. The instructions generate a universal image representation of the target image. The universal image representation based on latent variables generated by applying an autoencoder that generates latent variables for a multimodal graph representation of the target image. The instructions apply a machine learning algorithm to a feature vector based on the universal image representation to generate the classification for the target image. In some embodiments, the instructions to generate a universal image representation identify segments of the target image that correspond to regions of interest, generate the multimodal graph that includes vertices and edges where each vertex representing a segment and each edge representing a relationship between the segments represented by the vertices connected by the edge, generate subgraphs of the multimodal graph that include a home vertex and neighboring vertices representing segments of the target image, and apply an autoencoder to each subgraph to generate latent variables to represent the subgraph. In some embodiments, the instructions further train the machine learning algorithm for classification of images using training data that includes universal image representations of images and classifications of the images.

In some embodiments, one or more computing systems for generating training a machine learning algorithm to classify images are provided. The one or more computing systems include one or more computer-readable storage mediums and computer-executable instructions and one or more processors for executing the computer-executable instructions stored in the one or more computer-readable storage mediums. The instructions access training data that includes feature vectors including data derived from universal image representations of training images, each feature vector labeled with a classification. The universal image representation of a training image is derived from latent variables. The latent variables are generated by an autoencoder trained based on autoencoder training images. The instructions train the machine learning algorithm using the training data. In some embodiments, the autoencoder is trained based on subgraphs of a multimodal graph representation of the autoencoder training images. In some embodiments, the machine learning algorithm is a support vector machine. In some embodiments, the machine learning algorithm is a neural network. In some embodiments, the latent variables are generated by instructions that for each of a plurality of training images. The instructions identify segments of the training image, each segment associated with an attribute. The instructions generate a graph for the training image that includes vertices and edges. Each vertex represents a segment and each edge representing a relationship between the segments represented by the vertices connected by the edge. The instructions generate subgraphs of the graph that include a home vertex and neighboring vertices representing segments of the target image. The instructions apply the autoencoder to the subgraphs to generate the latent variables.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

We claim:

1. A method performed by one or more computing systems for classifying a target image with segments having attributes, the method comprising:
   identifying segments of the target image;
   generating a graph for the target image that includes vertices and edges, each vertex representing a segment and each edge satisfying an edge criterion based on the vertices that the edge connects, each vertex being assigned an attribute of the segment represented by the vertex;
   for each vertex, generating a subgraph that includes the vertex as a home vertex and neighboring vertices representing segments of the target image within a neighborhood of the segment represented by the home vertex, the vertices of the subgraph satisfying a neighborhood criterion;
   for each subgraph, applying an autoencoder to the subgraph to generate latent variables to represent the subgraph, the autoencoder being trained using subgraphs generated from images and attributes of segments of images of autoencoder training data; and
   applying a machine learning algorithm to a feature vector derived from the generated latent variables of the subgraphs to generate a classification for the target image, the machine learning algorithm being trained using feature vectors representing latent variables and labels representing classifications, the latent variables generated by applying the autoencoder to subgraphs for images and attributes of classification machine learning algorithm training data.

2. The method of claim 1 wherein the segments satisfy a segment criterion.

3. The method of claim 1 wherein the machine learning algorithm is a support vector machine.

4. The method of claim 1 wherein the machine learning algorithm is a neural network.

5. The method of claim 1 wherein the images are of cell cultures and the segments are cells, an attribute indicates whether the segment represented by a vertex is cancerous, and a classification indicates aggressiveness of cancer associated with the cell culture.

6. The method of claim 1 wherein the images are of a roadway system and each segment is a section of a roadway, an attribute indicates whether the segment represented by a vertex is congested, and a classification indicates whether action is needed to alleviate congestion.

7. The method of claim 1 wherein the images are of crowds and each segment is a person, an attribute indicates whether the segment represented by a vertex is of a person on a tracking list, and a classification indicates likelihood that an undesirable activity is in progress.

8. The method of claim 1 wherein the neighborhood criterion is based on distances between a segment represented by a home vertex and other segments.

9. The method of claim 1 wherein the neighborhood criterion is based on segments adjacent to the segment represented by the home vertex.

10. The method of claim 9 wherein the edges connect vertices representing adjacent segments and the neighborhood criterion is further based on edge distance from the home vertex.

11. The method of claim 1 further comprising generating a universal image representation of the target images, the universal image representation being derived from the generated latent variables.

12. One or more computing systems for classifying a target image with segments having attributes, the one or more computing systems comprising:
   one or more computer-readable storage mediums storing computer-executable instructions for controlling the one or more computing systems to:
      generate a graph represent the target image that includes vertices and edges, each vertex representing a portion of the target image and having an attribute;
      for each vertex, generate a subgraph that includes the vertex and neighboring vertices satisfying a neighborhood criterion;
      for each subgraph, apply an autoencoder to the subgraph to generate latent variables to represent the subgraph; and
      apply a machine learning algorithm to the latent variables of the subgraphs to generate a classification for the target image, the machine learning algorithm being trained using training latent variables representing training images and training classifications of the training images; and
   one or more processors for executing the computer-executable instructions stored in the one or more computer-readable storage mediums.

13. The one or more computing systems of claim 12 wherein the training latent variables are generated by applying the autoencoder to subgraphs of the graphs of the training images.

14. The one or more computing systems of claim 12 wherein the machine learning algorithm is a support vector machine.

15. The one or more computing systems of claim 12 wherein the machine learning algorithm is a neural network.

16. The one or more computing systems of claim 12 wherein an image is of a cell culture, the graph includes vertices representing one or more cells of the cell culture, each vertex having an attribute indicating whether the cells represented the vertex are cancerous, and a classification indicating aggressiveness of cancer associated with the cell culture.

17. The one or more computing systems of claim 12 wherein the images are of a roadway system, the graph having vertices representing sections of the roadway system, each vertex having an attribute indicating whether the section represented by the vertex is congested, and a classification indicating whether action is needed to alleviate congestion.

18. The one or more computing systems of claim 12 wherein the images are of crowds, the graph having vertices that each represent a person, each vertex having an attribute indicating whether the person represented by a vertex is of a person of interest, and a classification indicating likelihood that an activity of interest is in progress.

19. The one or more computing systems of claim 12 wherein the neighborhood criterion is based on distances between a home vertex and other vertices.

20. The one or more computing systems of claim 12 wherein the neighborhood criterion is based on vertices adjacent to the home vertex.

21. The one or more computing systems of claim 12 further comprising generating a universal image representation of the target image, the universal image representation being derived from the generated latent variables.

* * * * *